(12) United States Patent
Reynolds, III et al.

(10) Patent No.: US 7,799,309 B2
(45) Date of Patent: Sep. 21, 2010

(54) AREA WEIGHT UNIFORMITY FLEXIBLE GRAPHITE SHEET MATERIAL

(75) Inventors: Robert Anderson Reynolds, III, Bay Village, OH (US); Ronald Alfred Greinke, Medina, OH (US)

(73) Assignee: GrafTech International Holdings Inc., Parma, OH (US)

( * ) Notice: Subject to any disclaimer, the term of this patent is extended or adjusted under 35 U.S.C. 154(b) by 1211 days.

(21) Appl. No.: 10/496,715

(22) PCT Filed: Dec. 12, 2002

(86) PCT No.: PCT/US02/39749

§ 371 (c)(1),
(2), (4) Date: Jan. 18, 2005

(87) PCT Pub. No.: WO03/051772

PCT Pub. Date: Jun. 26, 2003

(65) Prior Publication Data

US 2005/0232845 A1    Oct. 20, 2005

(51) Int. Cl.
*C01B 31/04*    (2006.01)
(52) U.S. Cl. .................................................. 423/448
(58) Field of Classification Search ............... 423/448
See application file for complete search history.

(56) References Cited

U.S. PATENT DOCUMENTS

| | | | | |
|---|---|---|---|---|
| 3,404,061 A | * | 10/1968 | Shane et al. | 428/143 |
| 3,719,608 A | * | 3/1973 | Olstowski | 252/506 |
| 4,102,960 A | | 7/1978 | Borkowski | 264/42 |
| 4,895,713 A | | 1/1990 | Greinke et al. | 423/448 |
| 5,376,450 A | * | 12/1994 | Greinke et al. | 428/402 |
| 5,518,189 A | | 5/1996 | Grondin et al. | 241/20 |
| 6,149,972 A | | 11/2000 | Greinke | 427/220 |
| 2002/0168314 A1 | | 11/2002 | Roemmler | |

FOREIGN PATENT DOCUMENTS

| | | | |
|---|---|---|---|
| WO | WO 00/64808 | * | 11/2000 |
| WO | WO00/64808 A | | 11/2000 |

OTHER PUBLICATIONS

Hennig, Effects of Annealing on Radiation-Induced Lattice Vacancies in Natural Graphite Crystals, Applied Physics Letters 1964; 4(3): 55-56.*
Adjaye, et al., Production of hydrocarbons by catalytic upgrading of a fast pyrolysis of bio-oil. Part I: Conversion over various catalysts, Fuel Processing Technology 1995; 45: 161-183.*
International Publication No. WO 94/27909, filed May 21, 1993 by Lalancette.
McKay S F, "Expansion of annealed pyrolytic graphite," Journal of Applied Physics USA, vol. 35, No. 6, Jun. 1964.

* cited by examiner

*Primary Examiner*—Stanley S. Silverman
*Assistant Examiner*—Daniel C. McCracken
(74) *Attorney, Agent, or Firm*—Waddey & Patterson, P.C.; James R. Cartiglia

(57) ABSTRACT

A process for enhancing the expansion of intercalated graphite flake is presented. The process includes annealing the graphite flake at a temperature of at least about 3000° C. prior to intercalation and intercalating in the presence of a lubricious additive.

9 Claims, No Drawings

AREA WEIGHT UNIFORMITY FLEXIBLE GRAPHITE SHEET MATERIAL

TECHNICAL FIELD

The present invention relates to a flexible graphite sheet material which exhibits improved area weight uniformity, and processes for preparing the material. More particularly, processes of the present invention enable the production of sheet material that is thin yet exhibits the tensile strength and other characteristics necessary for handling and use of the sheets for a variety of applications.

BACKGROUND ART

Graphites are made up of layer planes of hexagonal arrays or networks of carbon atoms. These layer planes of hexagonally arranged carbon atoms are substantially flat and are oriented or ordered so as to be substantially parallel and equidistant to one another. The substantially flat, parallel equidistant sheets or layers of carbon atoms, usually referred to as graphene layers or basal planes, are linked or bonded together and groups thereof are arranged in crystallites. Highly ordered graphites consist of crystallites of considerable size: the crystallites being highly aligned or oriented with respect to each other and having well ordered carbon layers. In other words, highly ordered graphites have a high degree of preferred crystallite orientation. It should be noted that graphites possess anisotropic structures and thus exhibit or possess many properties that are highly directional such as thermal and electrical conductivity.

Graphites may be characterized as laminated structures of carbon, that is, structures consisting of superposed layers or laminae of carbon atoms joined together by weak van der Waals forces. In considering the graphite structure, two axes or directions are usually noted, to wit, the "c" axis or direction and the "a" axes or directions. For simplicity, the "c" axis or direction may be considered as the direction perpendicular to the carbon layers. The "a" axes or directions may be considered as the directions parallel to the carbon layers or the directions perpendicular to the "c" direction. The graphites suitable for manufacturing flexible graphite sheets possess a very high degree of orientation.

As noted above, the bonding forces holding the parallel layers of carbon atoms together are only weak van der Waals forces. Natural graphites can be treated so that the spacing between the superposed carbon layers or laminae can be appreciably opened up so as to provide a marked expansion in the direction perpendicular to the layers, that is, in the "c" direction, and thus form an expanded or intumesced graphite structure in which the laminar character of the carbon layers is substantially retained.

Graphite flake which has been greatly expanded and more particularly expanded so as to have a final thickness or "c" direction dimension which is as much as about 80 or more times the original "c" direction dimension can be formed without the use of a binder into cohesive or integrated sheets of expanded graphite, e.g. webs, papers, strips, tapes, foils, mats or the like (typically referred to as "flexible graphite"). The formation of graphite particles which have been expanded to have a final thickness or "c" dimension which is as much as about 80 times or more the original "c" direction dimension into integrated flexible sheets by compression, without the use of any binding material, is believed to be possible due to the mechanical interlocking, or cohesion, which is achieved between the voluminously expanded graphite particles.

In addition to flexibility, the sheet material, as noted above, has also been found to possess a high degree of anisotropy with respect to thermal and electrical conductivity due to orientation of the expanded graphite particles and graphite layers substantially parallel to the opposed faces of the sheet resulting from very high compression. Sheet material thus produced has excellent flexibility, good strength and a very high degree of orientation.

Briefly, the process of producing flexible, binderless anisotropic graphite sheet material, e.g. web, paper, strip, tape, foil, mat, or the like, comprises compressing or compacting under a predetermined load and in the absence of a binder, expanded graphite particles which have a "c" direction dimension which is as much as about 80 or more times that of the original particles so as to form a substantially flat, flexible, integrated graphite sheet. The expanded graphite particles that generally are worm-like or vermiform in appearance, once compressed, will maintain the compression set and alignment with the opposed major surfaces of the sheet. The density and thickness of the sheet material can be varied by controlling the degree of compression. The density of the sheet material can be within the range of from about 0.04 g/cc to about 2.0 g/cc. The flexible graphite sheet material exhibits an appreciable degree of anisotropy due to the alignment of graphite particles parallel to the major opposed, parallel surfaces of the sheet, with the degree of anisotropy increasing upon compression of the sheet material to increase orientation. In compressed anisotropic sheet material, the thickness, i.e. the direction perpendicular to the opposed, parallel sheet surfaces comprises the "c" direction and the directions ranging along the length and width, i.e. along or parallel to the opposed, major surfaces comprises the "a" directions and the thermal and electrical properties of the sheet are very different, by orders of magnitude, for the "c" and "a" directions.

As is appreciated in the art, however, graphites from different sources, such as various mines exhibit greatly varying degrees of expansion when intercalated and subjected to exfoliation. This is especially true of smaller particles (i.e., particles of 80 U.S. standard mesh or smaller). For this reason, certain sources of graphite, including certain sources of naturally occurring graphite, are excluded as a source material for many applications because of the poor expansion observed upon exfoliation.

DISCLOSURE OF THE INVENTION

It has been discovered in accordance with the present invention that when graphite flake is subjected to a preliminary annealing step, which involves heating to a temperature of at least about 3000° C., and intercalation effected in the presence of a lubricious additive, the graphite after subsequent exfoliation exhibits enhanced expansion, and that graphite flake from sources previously considered unacceptable by reason of poor expansion characteristics, achieves expansion comparable to that demonstrated by the flake from superior sources. Moreover, the resulting flexible graphite sheet material formed from the thusly-treated exfoliated graphite flakes exhibits higher area weight uniformity than graphite flakes treated in the conventional manner. By area weight uniformity is meant the weight of any given area of a flexible graphite sheet as compared with other same size areas of the sheet. The greater the uniformity in area weight of a sheet, the greater the tensile strength of the sheet. Thus, a flexible graphite sheet exhibiting relatively high area weight uniformity can be made thinner (even as thin as less than 3 mils, and as thin as 1 or 2 mils) with acceptable tensile strength (i.e., at least about 750 lbs/in$^2$) than more conventional flexible graphite sheets.

Typically, the area weight uniformity of a flexible graphite sheet is expressed as a percentage of density, when measured by dividing three times the standard deviation of the density by the average density. One way in which average weight density can be measured is by use of a beta scanner which scans over the sheet as it is being made. Beta particles are emitted on one side of the sheet and collected on the other. The graphite absorbs some of the beta particles based on the amount of graphite present. By calibration and monitoring the changes in the differences of the emitted compared to the absorbed beta particles one can determine the amount of graphite and hence the relative density.

It is an object of the invention to provide flexible graphite sheet having improved area weight uniformity.

It is another object of the invention to provide graphite flake which when intercalated will exhibit excellent expansion properties.

It is yet another object of the invention to provide graphite flake which when intercalated exhibits an enhanced and uniform degree of expansion.

It is a further object of the invention to provide a method for treating graphite flake prior to intercalation, which treatment facilitates the subsequent intercalation of flakes which heretofore had been considered too small to provide satisfactory expansion upon subsequent intercalation and exfoliation.

It is another object of the invention to provide a method for treating graphite flake, which treatment will result in enhanced expansion of flake and improved area weight uniformity when compressed into sheet form.

It is yet a further object of the invention to provide a method for treating graphite flake, which treatment will result in enhanced expansion of flake and, when compressed into sheet form, the ability to produce exceptionally thin sheets.

These and other objects are achieved by the invention which provides a method for forming particles of intercalated graphite flake having enhanced exfoliation volumes and improved area weight uniformity when compressed into sheet form. The method involves annealing graphite flake at a temperature in the range of at least about 3000° C. prior to intercalation and effecting intercalation in the presence of a lubricious additive.

BEST MODE FOR CARRYING OUT THE INVENTION

Graphite is a crystalline form of carbon comprising atoms covalently bonded in flat layered planes with weaker bonds between the planes. In obtaining source materials such as the above flexible sheets of graphite, particles of graphite, such as natural graphite flake, are typically treated with an intercalant of, e.g. a solution of sulfuric and nitric acid, the crystal structure of the graphite reacts to form a compound of graphite and the intercalant. The treated particles of graphite are hereafter referred to as "particles of intercalated graphite." Upon exposure to high temperature, the intercalant within the graphite decomposes and volatilizes, causing the particles of intercalated graphite to expand in dimension as much as about 80 or more times its original volume in an accordion-like fashion in the "c" direction, i.e. in the direction perpendicular to the crystalline planes of the graphite. The exfoliated graphite particles are vermiform in appearance, and are therefore commonly referred to as worms. The worms may be compressed together into flexible sheets that, unlike the original graphite flakes, can be formed and cut into various shapes and provided with small transverse openings by deforming mechanical impact.

Graphite starting materials for the flexible sheets suitable for use in the present invention include highly graphitic carbonaceous materials capable of intercalating organic and inorganic acids as well as halogens and then expanding when exposed to heat. These highly graphitic carbonaceous materials most preferably have a degree of graphitization of about 1.0. As used in this disclosure, the term "degree of graphitization" refers to the value g according to the formula:

$$g = \frac{3.45 - d(002)}{0.095}$$

where d(002) is the spacing between the graphitic layers of the carbons in the crystal structure measured in Angstrom units. The spacing d between graphite layers is measured by standard X-ray diffraction techniques. The positions of diffraction peaks corresponding to the (002), (004) and (006) Miller Indices are measured, and standard least squares techniques are employed to derive spacing which minimizes the total error for all of these peaks. Examples of highly graphitic carbonaceous materials include natural graphites from various sources, as well as other carbonaceous materials such as graphite prepared by chemical vapor deposition, high temperature pyrolysis of polymers, or crystallization from molten metal solutions, and the like. Natural graphite is most preferred.

The graphite starting materials for the flexible sheets used in the present invention may contain non-graphite components so long as the crystal structure of the starting materials maintains the required degree of graphitization and they are capable of exfoliation. Generally, any carbon-containing material, the crystal structure of which possesses the required degree of graphitization and which can be exfoliated, is suitable for use with the present invention. Such graphite preferably has an ash content of less than six weight percent. More preferably, the graphite employed for the present invention will have a purity of at least about 98%. In the most preferred embodiment, the graphite employed will have a purity of at least about 99%.

A common method for manufacturing graphite sheet is described by Shane et al. in U.S. Pat. No. 3,404,061, the disclosure of which is incorporated herein by reference. In the typical practice of the Shane et al. method, natural graphite flakes are intercalated by dispersing the flakes in a solution containing e.g., a mixture of nitric and sulfuric acid, advantageously at a level of about 20 to about 300 parts by weight of intercalant solution per 100 parts by weight of graphite flakes (pph). The intercalation solution contains oxidizing and other intercalating agents known in the art. Examples include those containing oxidizing agents and oxidizing mixtures, such as solutions containing nitric acid, potassium chlorate, chromic acid, potassium permanganate, potassium chromate, potassium dichromate, perchloric acid, and the like, or mixtures, such as for example, concentrated nitric acid and chlorate, chromic acid and phosphoric acid, sulfuric acid and nitric acid, or mixtures of a strong organic acid, e.g. trifluoroacetic acid, and a strong oxidizing agent soluble in the organic acid. Alternatively, an electric potential can be used to bring about oxidation of the graphite. Chemical species that can be introduced into the graphite crystal using electrolytic oxidation include sulfuric acid as well as other acids.

In a preferred embodiment, the intercalating agent is a solution of a mixture of sulfuric acid, or sulfuric acid and phosphoric acid, and an oxidizing agent, i.e. nitric acid, perchloric acid, chromic acid, potassium permanganate, hydrogen peroxide, iodic or periodic acids, or the like. Although less preferred, the intercalation solution may contain metal halides such as ferric chloride, and ferric chloride mixed with sulfuric acid, or a halide, such as bromine as a solution of bromine and sulfuric acid or bromine in an organic solvent.

The quantity of intercalation solution may range from about 20 to about 350 pph and more typically about 40 to about 160 pph. After the flakes are intercalated, any excess solution is drained from the flakes and the flakes are water-washed.

Alternatively, the quantity of the intercalation solution may be limited to between about 10 and about 40 pph, which permits the washing step to be eliminated as taught and described in U.S. Pat. No. 4,895,713, the disclosure of which is also herein incorporated by reference.

The particles of graphite flake treated with intercalation solution can optionally be contacted, e.g. by blending, with a reducing organic agent selected from alcohols, sugars, aldehydes and esters which are reactive with the surface film of oxidizing intercalating solution at temperatures in the range of 25° C. and 125° C. Suitable specific organic agents include hexadecanol, octadecanol, 1-octanol, 2-octanol, decylalcohol, 1,10 decanediol, decylaldehyde, 1-propanol, 1,3 propanediol, ethyleneglycol, polypropylene glycol dextrose, fructose, lactose, sucrose, potato starch, ethylene glycol monostearate, diethylene glycol dibenzoate, propylene glycol monostearate, glycerol monostearate, dimethyl oxylate, diethyl oxylate, methyl formate, ethyl formate, ascorbic acid and lignin-derived compounds, such as sodium lignosulfate. The amount of organic reducing agent is suitably from about 0.5 to 4% by weight of the particles of graphite flake.

The use of an expansion aid applied prior to, during or immediately after intercalation can also provide improvements. Among these improvements can be reduced exfoliation temperature and increased expanded volume (also referred to as "worm volume"). An expansion aid in this context will advantageously be an organic material sufficiently soluble in the intercalation solution to achieve an improvement in expansion. More narrowly, organic materials of this type that contain carbon, hydrogen and oxygen, preferably exclusively, may be employed. Carboxylic acids have been found especially effective, most preferably non-halogenated carboxylic acids.

A suitable carboxylic acid useful as the expansion aid can be selected from aromatic, aliphatic or cycloaliphatic, straight chain or branched chain, saturated and unsaturated monocarboxylic acids, dicarboxylic acids and polycarboxylic acids which have at least 1 carbon atom, and preferably up to about 15 carbon atoms, which is soluble in the intercalation solution in amounts effective to provide a measurable improvement of one or more aspects of exfoliation. Suitable organic solvents can be employed to improve solubility of an organic expansion aid in the intercalation solution.

Representative examples of saturated aliphatic carboxylic acids are acids such as those of the formula $H(CH_2)_nCOOH$ wherein n is a number of from 0 to about 5, including formic, acetic, propionic, butyric, pentanoic, hexanoic, and the like. In place of the carboxylic acids, the anhydrides or reactive carboxylic acid derivatives such as alkyl esters can also be employed. Representative of alkyl esters are methyl formate and ethyl formate. Sulfric acid, nitric acid and other known aqueous intercalants have the ability to decompose formic acid, ultimately to water and carbon dioxide. Because of this, formic acid and other sensitive expansion aids are advantageously contacted with the graphite flake prior to immersion of the flake in aqueous intercalant. Representative of dicarboxylic acids are aliphatic dicarboxylic acids having 2-12 carbon atoms, in particular oxalic acid, fumaric acid, malonic acid, maleic acid, succinic acid, glutaric acid, adipic acid, 1,5-pentanedicarboxylic acid, 1,6-hexanedicarboxylic acid, 1,10-decanedicarboxylic acid, cyclohexane-1,4-dicarboxylic acid and aromatic dicarboxylic acids such as phthalic acid or terephthalic acid. Representative of alkyl esters are dimethyl oxylate and diethyl oxylate. Representative of cycloaliphatic acids is cyclohexane carboxylic acid and of aromatic carboxylic acids are benzoic acid, naphthoic acid, anthranilic acid, p-aminobenzoic acid, salicylic acid, o-, m- and p-tolyl acids, methoxy and ethoxybenzoic acids, acetoacetamidobenzoic acids and, acetamidobenzoic acids, phenylacetic acid and naphthoic acids. Representative of hydroxy aromatic acids are hydroxybenzoic acid, 3-hydroxy-1-naphthoic acid, 3-hydroxy-2-naphthoic acid, 4-hydroxy-2-naphthoic acid, 5-hydroxy-1-naphthoic acid, 5-hydroxy-2-naphthoic acid, 6-hydroxy-2-naphthoic acid and 7-hydroxy-2-naphthoic acid. Prominent among the polycarboxylic acids is citric acid.

The intercalation solution will be aqueous and will preferably contain an amount of expansion aid of from about 1 to 10%, the amount being effective to enhance exfoliation. In the embodiment wherein the expansion aid is contacted with the graphite flake prior to or after immersing in the aqueous intercalation solution, the expansion aid can be admixed with the graphite by suitable means, such as a V-blender, typically in an amount of from about 0.2% to about 10% by weight of the graphite flake.

After intercalating the graphite flake, and following the blending of the intercalant coated intercalated graphite flake with the organic reducing agent, the blend can be exposed to temperatures in the range of 25° to 125° C. to promote reaction of the reducing agent and intercalant coating. The heating period is up to about 20 hours, with shorter heating periods, e.g., at least about 10 minutes, for higher temperatures in the above-noted range. Times of one-half hour or less, e.g., on the order of 10 to 25 minutes, can be employed at the higher temperatures.

The thus treated particles of graphite are sometimes referred to as "particles of intercalated graphite." Upon exposure to high temperature, e.g. temperatures of at least about 160° C. and especially about 700° C. to 1000° C. and higher, the particles of intercalated graphite expand as much as about 80 to 1000 or more times their original volume in an accordion-like fashion in the c-direction, i.e. in the direction perpendicular to the crystalline planes of the constituent graphite particles. The expanded, i.e. exfoliated, graphite particles are vermiform in appearance, and are therefore commonly referred to as worms. The worms may be compressed together into flexible sheets having small transverse openings that, unlike the original graphite flakes, can be formed and cut into various shapes, as hereinafter described. Compression can be effected by, e.g., compression molding, calendering, or other compression processes effective for formation of expanded graphite worms into coherent sheets.

Flexible graphite sheet and foil are coherent, with good handling strength, and are suitably compressed, e.g. compression molding, to a thickness of about 0.075 mm to 3.75 mm and a typical density of about 0.1 to 1.5 grams per cubic centimeter (g/cc). From about 1.5-30% by weight of ceramic additives can be blended with the intercalated graphite flakes as described in U.S. Pat. No. 5,902,762 (which is incorporated herein by reference) to provide enhanced resin impregnation in the final flexible graphite product. The additives include ceramic fiber particles having a length of about 0.15 to 1.5 millimeters. The width of the particles is suitably from about 0.04 to 0.004 mm. The ceramic fiber particles are non-reactive and non-adhering to graphite and are stable at temperatures up to about 1100° C., preferably about 1400° C. or higher. Suitable ceramic fiber particles are formed of macerated quartz glass fibers, carbon and graphite fibers, zirconia, boron nitride, silicon carbide and magnesia fibers, naturally occurring mineral fibers such as calcium metasilicate fibers, calcium aluminum silicate fibers, aluminum oxide fibers and the like.

The flexible graphite sheet can also, at times, be advantageously treated with resin and the absorbed resin, after curing, enhances the moisture resistance and handling strength, i.e. stiffness, of the flexible graphite sheet as well as "fixing" the morphology of the sheet. Suitable resin content is preferably at least about 5% by weight, more preferably about 10 to 35% by weight, and suitably up to about 60% by weight. Resins found especially useful in the practice of the present invention include acrylic-, epoxy- and phenolic-based resin systems, or mixtures thereof. Suitable epoxy resin systems include those based on diglycidyl ether or bisphenol A (DGEBA) and other multifunctional resin systems; phenolic resins that can be employed include resole and novolak phenolics.

The present invention is based on the discovery that the above described methods for intercalating and exfoliating graphite flake may beneficially be augmented by a pretreatment of the graphite flake at graphitization temperatures, i.e. temperatures in the range of about 3000° C. and above and by the inclusion in the intercalant of a lubricious additive. The pretreatment, or annealing, of the graphite flake results in significantly increased expansion (i.e., increase in expansion volume of up to 300% or greater) when the flake is subsequently subjected to intercalation and exfoliation. Indeed, desirably, the increase in expansion is at least about 50%, as compared to similar processing without the annealing step.

The annealing of the present invention is performed for a period of time sufficient to result in a flake having an enhanced degree of expansion upon intercalation and subsequent exfoliation. Typically the time required will be 1 hour or more, preferably 1 to 3 hours and will most advantageously proceed in an inert environment. The annealed graphite flake can also be subjected to other processes to enhance the degree of expansion—namely intercalation in the presence of an organic reducing agent, an intercalation aid such as an organic acid, and a surfactant wash following intercalation. Moreover, for maximum beneficial results, the intercalation step may be repeated.

The annealing step of the instant invention may be performed in an induction furnace or other such apparatus, such as those furnaces employed for the production of synthetic graphite from coke/pitch mixtures.

Because it has been observed that the worms produced using graphite subjected to pre-intercalation annealing can sometimes "clump" together, which can negatively impact area weight uniformity, an additive that assists in the formation of "free flowing" worms is highly desirable. The addition of a lubricious additive to the intercalation solution facilitates the more uniform distribution of the worms across the bed of a compression apparatus (such as the bed of a calender station conventionally used for compressing (or "calendering") graphite worms into flexible graphite sheet. The resulting sheet therefore has higher area weight uniformity and greater tensile strength, even when the starting graphite particles are as small as 200 U.S. mesh or smaller. The lubricious additive is preferably a long chain hydrocarbon, more preferably a hydrocarbon having at least about 10 carbons. Other organic compounds having long chain hydrocarbon groups, even if other functional groups are present, can also be employed.

More preferably, the lubricious additive is an oil, with a mineral oil being most preferred, especially considering the fact that mineral oils are less prone to rancidity and odors, which can be an important consideration for long term storage. It will be noted that certain of the expansion aids detailed above also meet the definition of a lubricious additive. When these materials are used as the expansion aid, it may not be necessary to include a separate lubricious additive in the intercalant.

The lubricious additive is present in the intercalant in an amount of at least about 1.4 pph, more preferably at least about 1.8 pph. Although the upper limit of the inclusion of lubricous additive is not as critical as the lower limit, there does not appear to be any significant additional advantage to including the lubricious additive at a level of greater than about 4 pph. Although it is preferable to add the lubricious additive during intercalation, it can also be applied to the graphite during or after the washing or drying steps.

As is appreciated in the art, natural graphite from many mines has heretofore been considered unsatisfactory, or of marginal utility, for many applications, for the graphite flake from those sources did not undergo satisfactory expansion when subjected to conventional intercalation and exfoliation. When subjected to the above described processing, however, graphite flake from sources previously considered unsatisfactory becomes usable. In fact, when subjected to the procedure of the instant invention, graphite flake from a full range of natural sources achieves a uniform and unexpectedly enhanced degree of expansion and can be used to form flexible graphite sheet having an unexpectedly high area weight uniformity.

In addition to providing uniform and enhanced expansion of graphite from all sources, the inventive procedures permit satisfactory intercalation and exfoliation of smaller particle size natural graphite then had heretofore had been deemed suitable for intercalation and exfoliation owing to poor expansion. Following the process of the present invention, intercalating and exfoliation of small graphite flake can be made to yield a unique expanded graphite product.

The invention thus being described, it will be obvious that it may be varied in many ways. Such variations are not to be regarded as a departure from the spirit and scope of the present invention and all such modifications as would be obvious to one skilled in the art are intended to be included within the scope of the following claims.

What is claimed is:

1. A process for preparing flexible graphite sheet having a thickness of less than 3 mils and a tensile strength of at least about 750 lbs/in$^2$, comprising:
   (1) treating natural graphite flakes with an intercalant comprising a lubricious additive to provide intercalated graphite flakes;
   (2) exfoliating the intercalated graphite flakes to form exfoliated graphite flakes; and
   (3) thereafter forming the exfoliated graphite flakes into a flexible graphite sheet.

2. The process of claim 1 wherein the flexible graphite sheet is no more than 2 mils thick.

3. The process of claim 1, which further comprises annealing the graphite flakes at a temperature of at least about 3000° C. prior to treatment with the intercalant.

4. The process claim of claim 3 wherein the annealing is performed for a period in excess of 1 hour.

5. The process of claim 4 wherein the annealing is performed in an inert environment.

6. The process of claim 1 wherein the lubricious additive is present in the intercalant at a level of at least about 1.4 pph.

7. The process of claim 6 wherein the lubricious additive comprises a long chain hydrocarbon or long chain hydrocarbon group.

8. The process of claim 7 wherein the lubricious additive comprises an oil.

9. The process of claim 7 wherein the lubricious additive comprises a hydrocarbon having at least 10 carbons.

* * * * *